United States Patent
Kitano et al.

(10) Patent No.: US 10,595,718 B2
(45) Date of Patent: Mar. 24, 2020

(54) ENDOSCOPE

(71) Applicant: FUJIFILM Corporation, Tokyo (JP)

(72) Inventors: Ryo Kitano, Kanagawa (JP); Shinichiro Sonoda, Kanagawa (JP); Takashi Yano, Kanagawa (JP); Eiji Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 325 days.

(21) Appl. No.: 15/614,621

(22) Filed: Jun. 6, 2017

(65) Prior Publication Data

US 2018/0008133 A1 Jan. 11, 2018

(30) Foreign Application Priority Data

Jul. 11, 2016 (JP) ................ 2016-136913

(51) Int. Cl.
*A61B 1/05* (2006.01)
*H04N 5/225* (2006.01)
(Continued)

(52) U.S. Cl.
CPC .......... *A61B 1/051* (2013.01); *A61B 1/00096* (2013.01); *A61B 1/00124* (2013.01);
(Continued)

(58) Field of Classification Search
CPC . A61B 1/00096; A61B 1/051; A61B 1/00124; H04N 5/2253; H04N 5/2257;
(Continued)

(56) References Cited

U.S. PATENT DOCUMENTS

| 6,567,115 B1 | 5/2003 | Miyashita et al. |
| 9,411,150 B2 | 8/2016 | Nagase |
| (Continued) | | |

FOREIGN PATENT DOCUMENTS

| JP | H04327827 | 11/1992 |
| JP | H0938031 | 2/1997 |
| (Continued) | | |

OTHER PUBLICATIONS

"Office Action of Japan Counterpart Application", dated May 7, 2019, with English translation thereof, p. 1-p. 5.
(Continued)

*Primary Examiner* — Aaron B Fairchild
(74) *Attorney, Agent, or Firm* — JCIPRNET (57) ABSTRACT

The endoscope includes an imaging device that is provided in a tip portion of an insertion part capable of being inserted into a body cavity. The imaging device includes an image sensor that photoelectrically converts imaging light incident on an image receiving surface thereof through an imaging lens provided in a lens barrel, and a circuit substrate including a connecting surface facing a terminal face that is a surface opposite to the image receiving surface of the image sensor. A plurality of terminals are uniformly arranged longitudinally and laterally in a two-dimensional matrix form on the terminal face of the image sensor, and the connecting surface of the circuit substrate and the terminal face of the image sensor are connected to each other through the plurality of terminals. The total area of the plurality of terminals on the terminal face occupies 10% or more of the area of an imaging area of the image receiving surface.

13 Claims, 7 Drawing Sheets

(51) Int. Cl.
*A61B 1/00* (2006.01)
*A61B 1/005* (2006.01)
*A61B 1/06* (2006.01)

(52) U.S. Cl.
CPC ............ *H04N 5/2253* (2013.01); *A61B 1/005* (2013.01); *A61B 1/00101* (2013.01); *A61B 1/053* (2013.01); *A61B 1/0661* (2013.01); *H05K 2201/10378* (2013.01)

(58) Field of Classification Search
CPC ........ H04N 5/2258; H05K 2201/10378; H01L 27/14636; H01L 2924/00
See application file for complete search history.

(56) References Cited

U.S. PATENT DOCUMENTS

| | | | | |
|---|---|---|---|---|
| 2005/0267328 | A1* | 12/2005 | Blumzvig | A61B 1/00096 600/109 |
| 2010/0261961 | A1* | 10/2010 | Scott | A61B 1/00193 600/111 |
| 2011/0245600 | A1 | 10/2011 | Ishii et al. | |
| 2015/0065798 | A1 | 3/2015 | Kuroda | |
| 2015/0293343 | A1* | 10/2015 | Nagase | A61B 1/051 348/76 |

FOREIGN PATENT DOCUMENTS

| | | |
|---|---|---|
| JP | 2000199863 | 7/2000 |
| JP | 2013244252 | 12/2013 |
| JP | 2016-006880 | 1/2016 |
| WO | 2010081137 | 7/2010 |
| WO | 2015019669 | 2/2015 |

OTHER PUBLICATIONS

"Office Action of Europe Counterpart Application", dated May 20, 2019, p. 1-p. 4.

"Search Report of European Counterpart Application," dated Dec. 5, 2017, p. 1-p. 8.

"Office Action of Europe Counterpart Application", dated Sep. 25, 2018, p. 1-p. 6.

* cited by examiner

ENDOSCOPE

CROSS-REFERENCE TO RELATED APPLICATIONS

The present application claims priority under 35 U.S.C. § 119 to Japanese Patent Application No. 2016-136913, filed on Jul. 11, 2016. Each of the above application(s) is hereby expressly incorporated by reference, in its entirety, into the present application.

BACKGROUND OF THE INVENTION

1. Field of the Invention

The present invention relates to an endoscope.

2. Description of the Related Art

An imaging device, which is mounted in a tip portion of an insertion part of an endoscope, generally includes a solid-state imaging element and a circuit substrate on which the solid-state imaging element is mounted. The solid-state imaging element is connected to a terminal portion of the circuit substrate by an ACF (anisotropic conductive film) or the like (see JP2016-6880A). Further, a plurality of transmission cables, which are connected to a processor unit and the like, are connected to the circuit substrate.

SUMMARY OF THE INVENTION

The solid-state imaging element, which is used in the imaging device of the endoscope, tends to be significantly reduced in size, and a solid-state imaging element having a size of 1 square millimeter is also put to practical use at present. As the solid-state imaging element is reduced in size as described above, the area of a connecting portion between the solid-state imaging element and the circuit substrate on which the element is mounted is reduced. As a result, if the connection strength between the solid-state imaging element and the circuit substrate is not sufficiently ensured, there is a possibility that the connecting portion may be separated due to a load applied at the time of a manufacturing process or an angle operation of the endoscope.

The invention has been made in consideration of the above-mentioned circumstances, and an object of the invention is to provide an endoscope in which connection strength between a solid-state imaging element and a circuit substrate can be sufficiently ensured.

An endoscope according to an aspect of the invention comprises an imaging device that is provided in a tip portion of an insertion part capable of being inserted into a body cavity. The imaging device includes a solid-state imaging element that photoelectrically converts imaging light incident on an image receiving surface thereof through an imaging lens, and a circuit substrate including a connecting surface facing a terminal face that is a surface opposite to the image receiving surface of the solid-state imaging element. A plurality of terminals are uniformly arranged longitudinally and laterally in a two-dimensional matrix form on the terminal face of the solid-state imaging element, the connecting surface of the circuit substrate and the terminal face of the solid-state imaging element are connected to each other through the plurality of terminals, and the total area of the plurality of terminals, which are arranged on the terminal face, occupies 10% or more of the area of an imaging area of the image receiving surface of the solid-state imaging element.

According to the invention, it is possible to provide an endoscope that can sufficiently ensure connection strength between a solid-state imaging element and a circuit substrate.

DESCRIPTION OF THE PREFERRED EMBODIMENTS

An embodiment of the invention will be described below with reference to the drawings.

Figure 1:
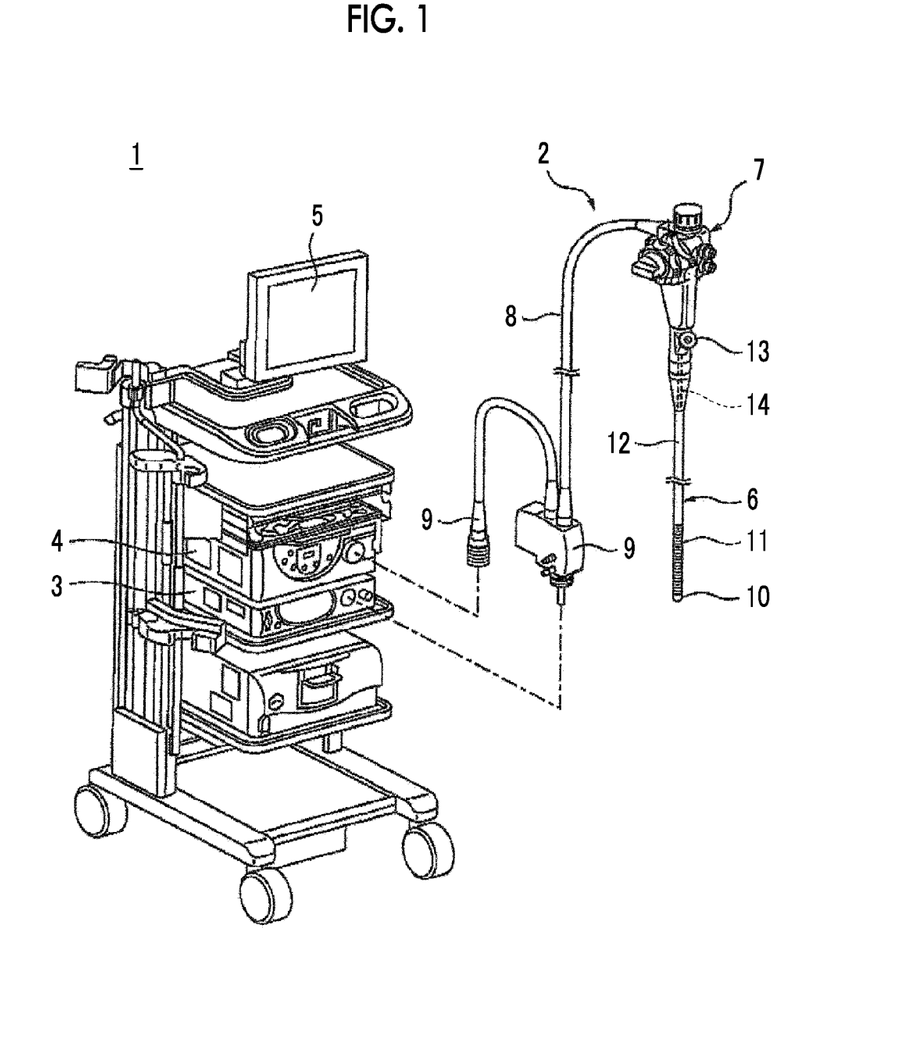
FIG. 1 is a view showing the structure of an example of an endoscope system that is used to illustrate an embodiment of the invention.

FIG. 1 shows an example of an endoscope system that is used to illustrate the embodiment of the invention.

The endoscope system 1 includes an endoscope 2, a light source unit 3, and a processor unit 4. The endoscope 2 includes an insertion part 6 that is capable of being inserted into a subject, an operation unit 7 that is connected to the insertion part 6, and a universal cord 8 that extends from the operation unit 7. The insertion part 6 includes a tip portion 10, a bendable portion 11 that is connected to the tip portion 10, and a soft portion 12 that connects the bendable portion 11 to the operation unit 7.

An illumination optical system that emits illumination light for illuminating a portion to be observed, an imaging device and an imaging optical system that take an image of the portion to be observed, and the like are provided in the tip portion 10. The bendable portion 11 is adapted to be bendable in a direction perpendicular to the longitudinal axis of the insertion part 6, and an operation for bending the bendable portion 11 is manipulated by the operation unit 7. Further, the soft portion 12 is rather flexible so as to be deformable according to the shape of the insertion path of the insertion part 6.

The operation unit 7 is provided with a button that is used to manipulate an imaging operation of the imaging device provided in the tip portion 10, a knob that is used to manipulate a bending operation of the bendable portion 11, and the like. Further, the operation unit 7 is provided with an inlet 13 into which a treatment tool, such as an electric scalpel, is introduced, and a treatment tool channel 14, which reaches the tip portion 10 from the inlet 13 and into which the treatment tool is capable of being inserted, is provided in the insertion part 6.

A connector 9 is provided at the end of the universal cord 8, and the endoscope 2 is connected to the light source unit 3, which generates illumination light to be emitted from the illumination optical system provided in the tip portion 10, and the processor unit 4, which processes a video signal acquired by the imaging device provided in the tip portion 10, through the connector 9. The processor unit 4 generates the video data of the portion to be observed by processing the input video signal, displays the generated video data on a monitor 5, and records the generated video data.

A light guide and a wire group are housed in the insertion part 6, the operation unit 7, and the universal cord 8. The illumination light, which is generated by the light source unit 3, is guided to the illumination optical system, which is provided in the tip portion 10, through the light guide, and a signal and power are transmitted between the imaging device, which is provided in the tip portion 10, and the processor unit 4 through the wire group.

(First Example of Imaging Device)

Figure 2:
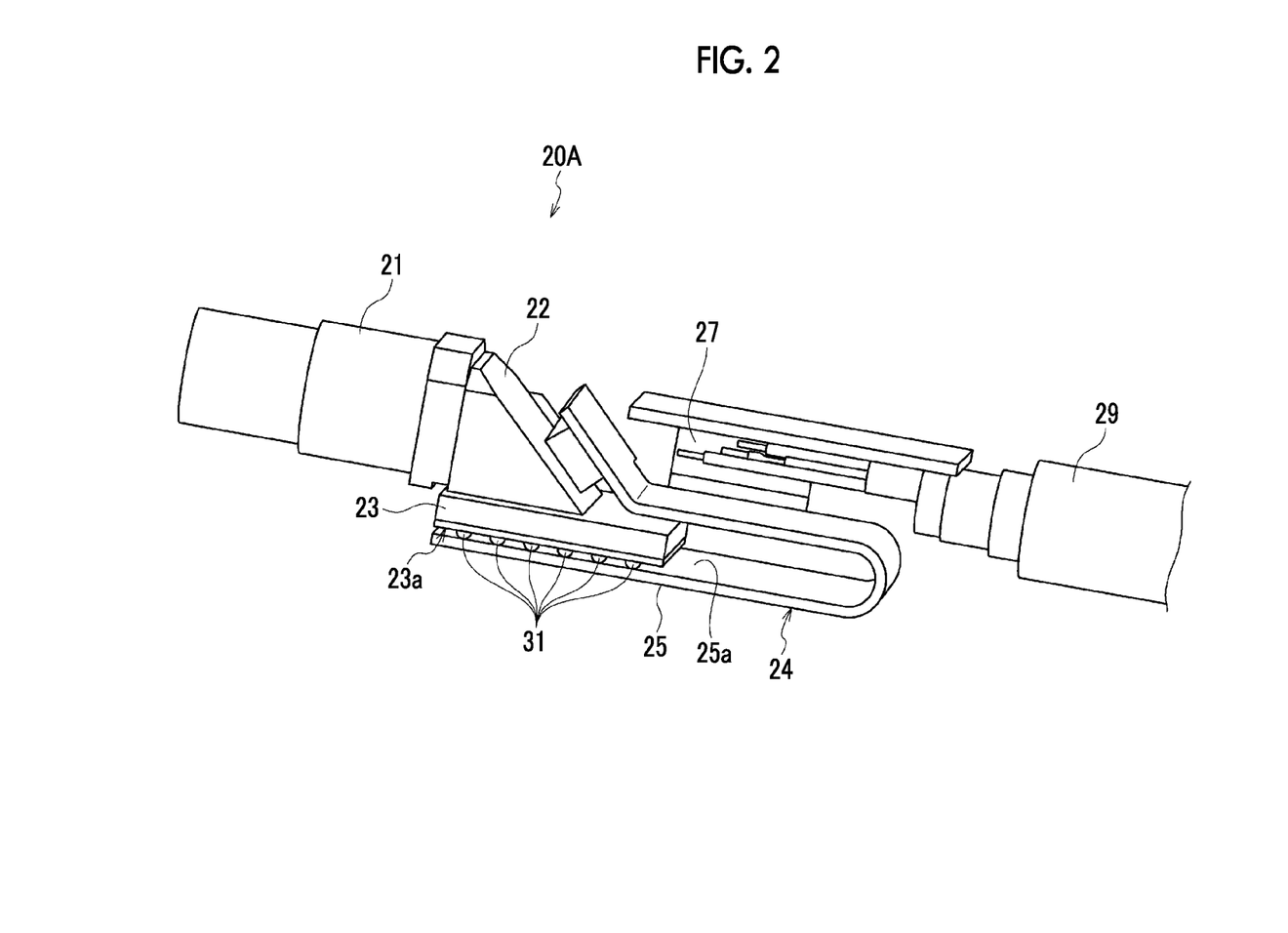
FIG. 2 is a view showing a first example of the structure of an imaging device that is mounted in a tip portion of an insertion part of the endoscope.
Figure 3:
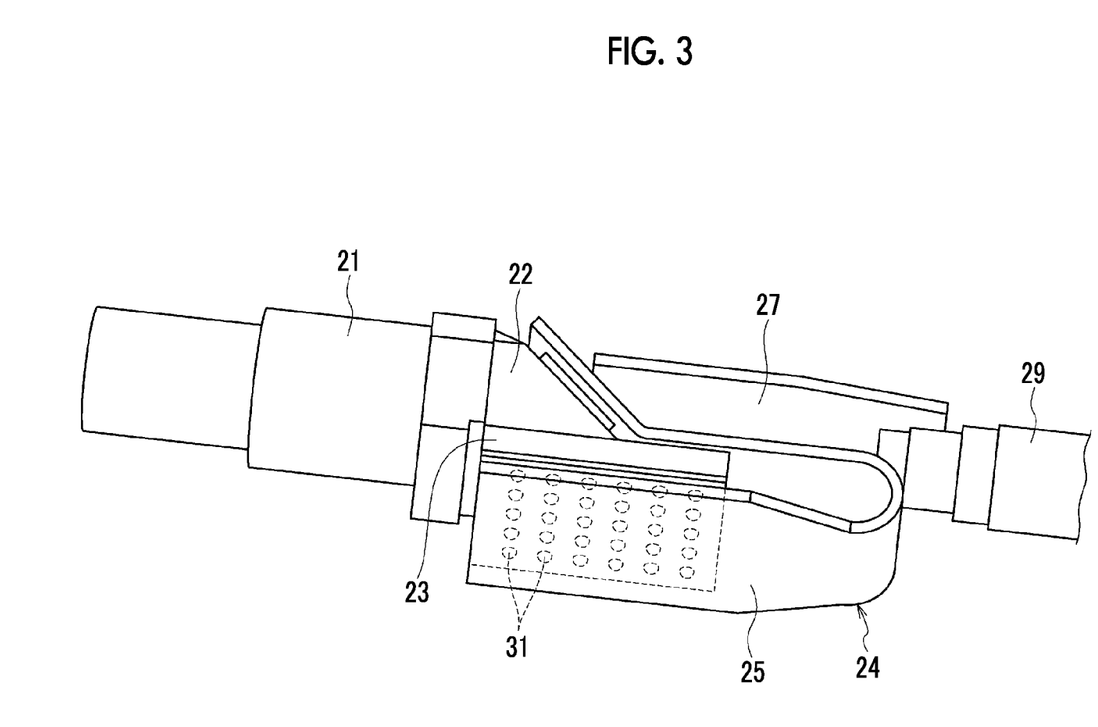
FIG. 3 is a view showing the first example of the structure of the imaging device that is mounted in the tip portion of the insertion part of the endoscope.

FIGS. 2 and 3 show a first example of the structure of the imaging device that is mounted in the tip portion 10 of the insertion part 6. An imaging device 20A shown in FIGS. 2 and 3 includes a lens barrel 21 that houses an imaging lens (not shown), a prism 22 on which imaging light having passed through the imaging lens is incident, an image sensor 23 that is mounted on the light emitting surface of the prism 22, and a circuit substrate 24 on which the image sensor 23 is mounted.

The prism 22 is a rectangular prism of which a light incident surface and a light emitting surface cross each other at a right angle.

The image sensor 23 is a solid-state imaging element, such as a CCD (Charge Coupled Device) image sensor or a CMOS (Complementary Metal Oxide Semiconductor) image sensor. The image sensor 23 is disposed such that the image receiving surface of the image sensor 23 faces the light emitting surface of the prism 22 and is parallel to the longitudinal direction of the insertion part 6. A plurality of hemispherical terminals 31 are uniformly arranged longitudinally and laterally in a two-dimensional matrix form on a terminal face 23a that is a surface opposite to the image receiving surface of the image sensor 23. That is, the terminal face 23a has the structure of BGA (Ball Grid Array), but may have the structure of LGA (Land Grid Array). The total area of the plurality of terminals 31, which are arranged on the terminal face 23a, occupies 10% or more of the area of the imaging area of the image receiving surface of the image sensor 23.

The circuit substrate 24 is a so-called flexible substrate having flexibility. The circuit substrate 24 includes an image sensor connecting portion 25 on which the image sensor 23 is mounted and a cable connecting portion 27 to which a transmission cable 29 is connected. The image sensor connecting portion 25 includes a connecting surface 25a that faces the terminal face 23a of the image sensor 23. Lands are formed on the connecting surface 25a at positions facing the respective terminals 31 of the image sensor 23. The image sensor 23 is mounted on the circuit substrate 24 and the terminals 31 of the image sensor 23 are connected to the lands of the circuit substrate 24 by solder, so that the connecting surface 25a of the circuit substrate 24 and the terminal face 23a of the image sensor 23 are electrically connected to each other.

According to the structure of the first example having been described above, the plurality of terminals 31, of which the total area occupies 10% or more with respect to the imaging area of the image sensor 23, are uniformly arranged longitudinally and laterally in a two-dimensional matrix form on the terminal face 23a of the image sensor 23, and the connecting surface 25a of the circuit substrate 24 and the terminal face 23a of the image sensor 23 are connected to each other through the plurality of terminals 31. For this reason, since the connecting area between the image sensor 23 and the circuit substrate 24 can be sufficiently ensured, the strength and reliability of the connection between the image sensor 23 and the circuit substrate 24 can be improved.

(Second Example of Imaging Device)

Figure 4:
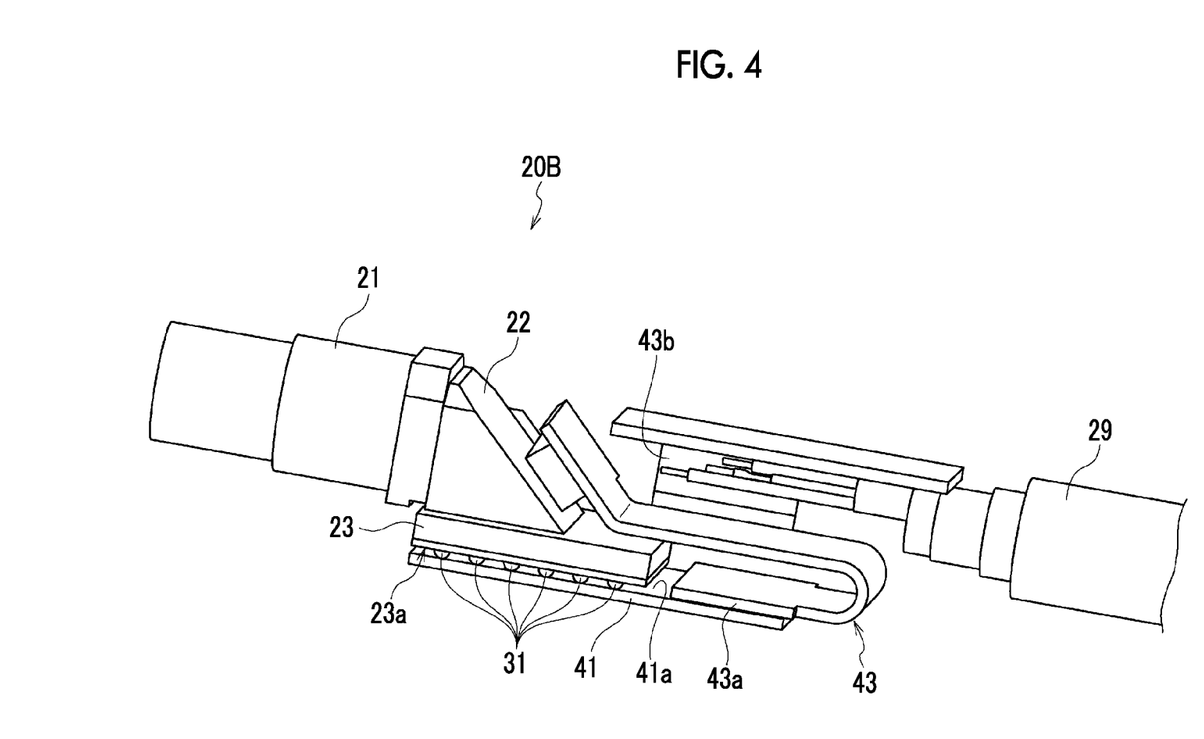
FIG. 4 is a view showing a second example of the structure of the imaging device that is mounted in the tip portion of the insertion part of the endoscope.

FIG. 4 shows a second example of the structure of the imaging device that is mounted in the tip portion 10 of the insertion part 6. The same components as the components of the imaging device 20A described in the first example or components equivalent to the components of the imaging device 20A are denoted by the same reference numerals as the reference numerals of the components of the imaging device 20A or corresponding reference numerals, and the description thereof will be simplified or omitted. An imaging device 20B shown in FIG. 4 includes a lens barrel 21, a prism 22, an image sensor 23, a circuit substrate 41 on which the image sensor 23 is mounted, and a flexible wiring substrate 43 to which a transmission cable 29 is connected. The lens barrel 21, the prism 22, and the image sensor 23 are the same as those of the first example.

The circuit substrate 41 is a rigid substrate of which the bending stiffness is higher than the bending stiffness of the image sensor 23. Further, it is preferable that the circuit substrate 41 is a ceramic substrate having a value of thermal expansion coefficient close to that of the thermal expansion coefficient of silicon or glass used for the substrate of the image sensor 23. Furthermore, the ceramic substrate has a modulus of elasticity higher than the modulus of elasticity of a glass epoxy substrate or the like used as the rigid substrate. For this reason, it is preferable that the circuit substrate 41 is a ceramic substrate since the circuit substrate 41 made of ceramics has high bending stiffness even though being thin.

The circuit substrate 41 has a connecting surface 41a facing a terminal face 23a of the image sensor 23. Lands are formed on the connecting surface 41a at positions facing the respective terminals 31 of the image sensor 23. The image sensor 23 is mounted on the circuit substrate 41 and the terminals 31 of the image sensor 23 are connected to the lands of the circuit substrate 41 by solder, so that the connecting surface 41a of the circuit substrate 41 and the terminal face 23a of the image sensor 23 are electrically connected to each other.

The flexible wiring substrate 43 is a so-called flexible substrate, and includes a substrate connecting portion 43a that is electrically connected to the circuit substrate 41 and a cable connecting portion 43b to which the transmission cable 29 is connected. The circuit substrate 41 and the flexible wiring substrate 43 are connected to each other at the substrate connecting portion 43a by solder or an ACF (anisotropic conductive film).

According to the structure of the second example having been described above, the circuit substrate 41 to which the image sensor 23 is connected is a rigid substrate of which the bending stiffness is higher than the bending stiffness of the image sensor 23. Accordingly, bending stress, which is generated at the time of an angle operation or the like of the endoscope, is not applied to the connecting portion between the image sensor 23 and the circuit substrate 41. Therefore, the reliability of the connection between the image sensor 23 and the circuit substrate 24 can be improved.

Further, since the circuit substrate 41 is a ceramic substrate having a value of thermal expansion coefficient close to that of the thermal expansion coefficient of silicon or glass used for the substrate of the image sensor 23, the expansion or contraction of the image sensor 23, which is caused by a change in temperature when the image sensor 23 is mounted on the circuit substrate 41, is substantially the same as that of the circuit substrate 41. If the image sensor 23 is mounted on a flexible substrate that contains polyimide or the like, which has a thermal expansion coefficient larger than the thermal expansion coefficient of silicon or glass, as a main component, the substrate of the image sensor 23 is warped due to the deformation of the flexible substrate caused particularly at the time of cooling. For this reason, local distortion may be generated at the connecting portion between the image sensor 23 and the circuit substrate 41. However, according to the structure of the second example, a ceramic substrate, which has a thermal expansion coefficient close to the thermal expansion coefficient of the substrate of the image sensor 23 and high bending stiffness, is used as the circuit substrate 41. It is difficult for distortion having been described above to be generated when the image sensor 23 is mounted on the circuit substrate 41. As a result, since the image sensor 23 is uniformly connected to the circuit substrate 41, an unnecessary force is also not applied to the substrate of the image sensor 23. Therefore, the reliability of the connection between the image sensor 23 and the circuit substrate 24 can be improved.

(Third Example of Imaging Device)

Figure 5:
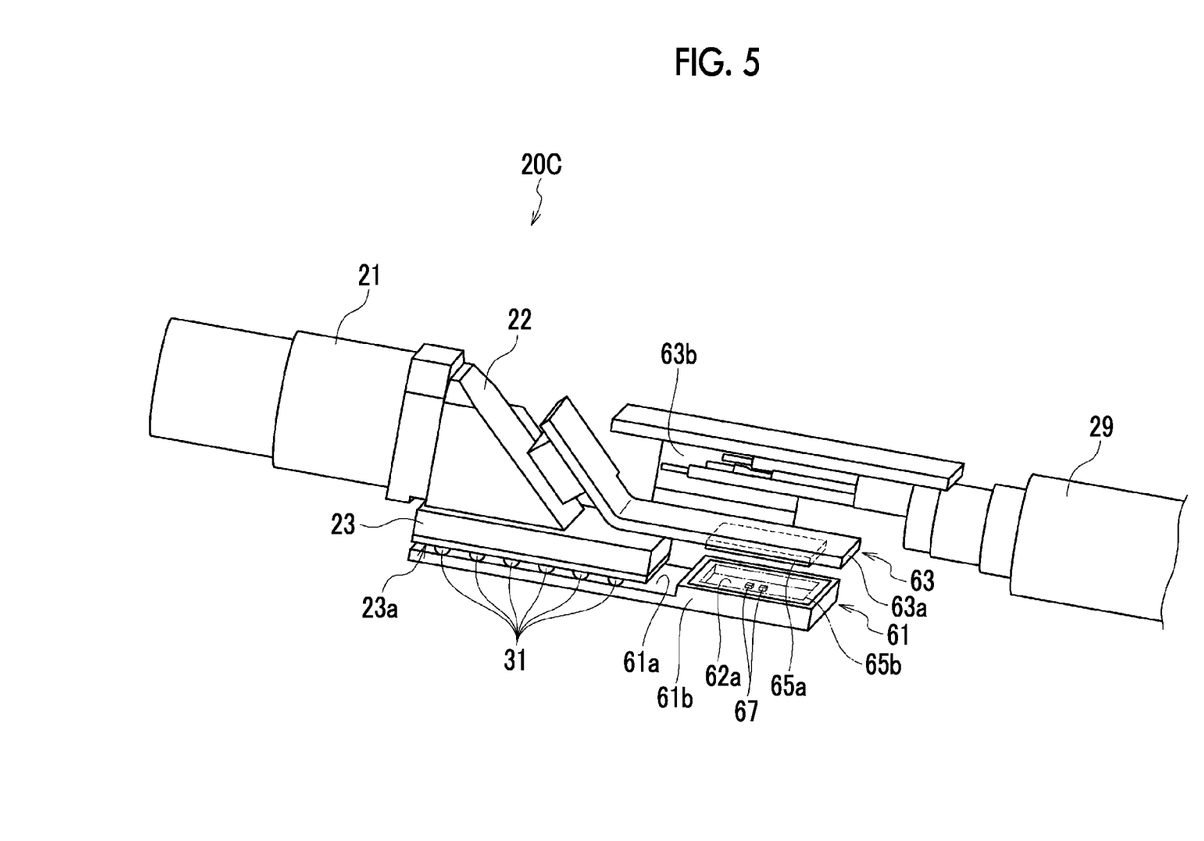
FIG. 5 is a view showing a third example of the structure of the imaging device that is mounted in the tip portion of the insertion part of the endoscope.

FIG. 5 shows a third example of the structure of the imaging device that is mounted in the tip portion 10 of the insertion part 6. The same components as the components of the imaging device 20B described in the second example or components equivalent to the components of the imaging device 20B are denoted by the same reference numerals as the reference numerals of the components of the imaging device 20B or corresponding reference numerals, and the description thereof will be simplified or omitted. An imaging device 20C shown in FIG. 5 includes a lens barrel 21, a prism 22, an image sensor 23, a circuit substrate 61 on which the image sensor 23 is mounted, a flexible wiring substrate 63 to which a transmission cable 29 is connected, and a pair of connectors 65 (a male connector 65a and a female connector 65b) that electrically connects the circuit substrate 61 to the flexible wiring substrate 63. The lens barrel 21, the prism 22, and the image sensor 23 are the same as those of the first or second example.

The circuit substrate 61 is a rigid substrate of which the bending stiffness is higher than the bending stiffness of the image sensor 23 and is a ceramic substrate as in the second example. The circuit substrate 61 includes a connecting surface 61a that faces a terminal face 23a of the image sensor 23 and a connector mounting portion 61b on which the female connector 65b is mounted. Lands are formed on the connecting surface 61a at positions facing the respective terminals 31 of the image sensor 23. The image sensor 23 is mounted on the circuit substrate 61 and the terminals 31 of the image sensor 23 are connected to the lands of the circuit substrate 61 by solder, so that the connecting surface 61a of the circuit substrate 61 and the terminal face 23a of the image sensor 23 are electrically connected to each other.

A recessed portion 62 on which the female connector 65b is mounted is formed on the connector mounting portion 61b of the circuit substrate 61, and a plurality of electrodes, which are to be electrically connected to electrodes of the female connector 65b, are formed on the upper surface of the recessed portion 62. Electronic components 67, such as a resistor and a capacitor, are mounted substantially at the center of the bottom surface of the recessed portion 62.

The flexible wiring substrate 63 is a so-called flexible substrate, and includes a substrate connecting portion 63a that is electrically connected to the circuit substrate 61 through the male connector 65a and a cable connecting portion 63b to which the transmission cable 29 is connected. The male connector 65a is mounted on the substrate connecting portion 63a.

Figure 6:
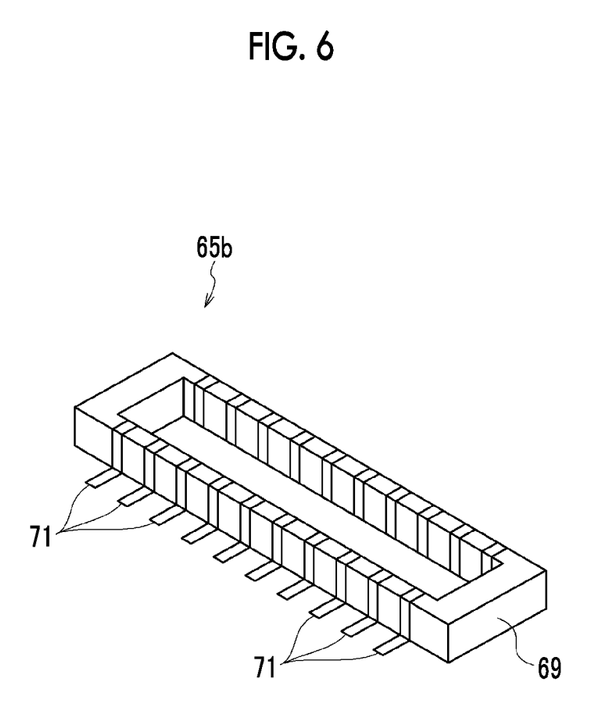
FIG. 6 is a perspective view of a connector that is included in the imaging device of the third example.

As shown in FIG. 6, the female connector 65b includes a rectangular flat plate-shaped connector body 69 which a recessed portion is provided at the center thereof and a plurality of electrodes 71 are provided on the long side portions of the connector body 69. The male connector 65a is fitted to the recessed portion that is provided in the connector body 69 of the female connector 65b. A recessed portion is also provided at the center of the male connector 65a. Since this recessed portion is provided in the male connector 65a, the electronic components 67 mounted in the recessed portion 62 of the connector mounting portion 61b do not interfere with the male connector 65a in a state in which the male connector 65a is fitted to the female connector 65b. Since electronic components can be mounted outside a region in which the circuit substrate 61 and the flexible wiring substrate 63 are connected to each other, the saving of a space corresponding to the disposition of the electronic components can be achieved.

According to the structure of the third example having been described above, since the circuit substrate 61 and the flexible wiring substrate 63 are connected to each other through the connectors 65, the reliability of the connection between the circuit substrate 61 and the flexible wiring substrate 63 and assembly easiness therebetween can be improved. If the circuit substrate 61 and the flexible wiring substrate 63 are connected to each other by solder or an ACF, there is a possibility that connection strength may be insufficient according to a connecting area. Further, if the circuit substrate 61 and the flexible wiring substrate 63 are connected to each other by an ACF and the circuit substrate 61 is made to be thin, the circuit substrate 61 pressed to be connected to the flexible wiring substrate 63 may be damaged. However, according to the structure of the third example, it is possible to achieve sufficient and highly reliable connection by only performing easy work for fitting the connector 65, which is mounted on the flexible wiring substrate 63, to the connector mounting portion 61b of the circuit substrate 61. Furthermore, since the connector 65 can also be removed from the connector mounting portion 61b of the circuit substrate 61, repairability is good.

In addition, since electronic components are disposed in the recessed portion 69a provided on the connector 65b, the size of the imaging device 20C can be reduced.

Figure 7:
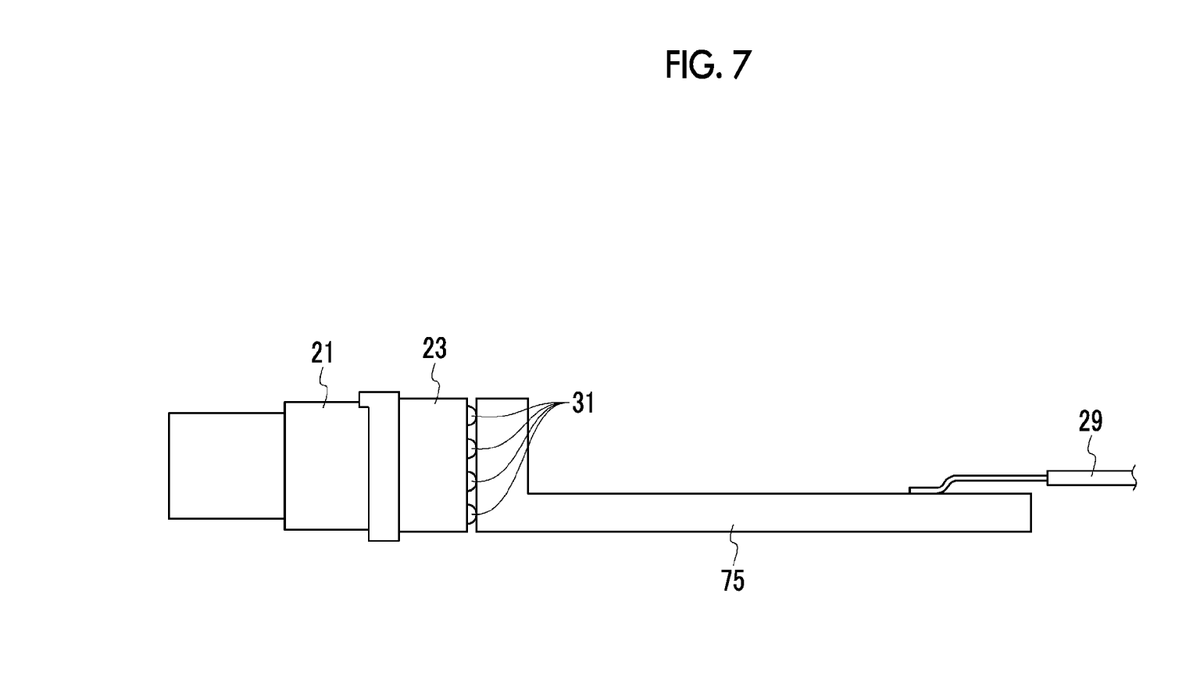
FIG. 7 is a side view showing another example of the structure of the imaging device.

Each of the above-mentioned imaging devices of the first to third examples includes the prism 22, and the image sensor 23 is disposed such that the image receiving surface of the image sensor 23 faces the light emitting surface of the prism 22 and is parallel to the longitudinal direction of the insertion part 6. Further, the image sensor 23 may be disposed such that the image receiving surface of the image sensor 23 is perpendicular to the longitudinal direction of the insertion part 6 as shown in FIG. 7. In this case, the imaging device is not provided with the prism 22, and the tip portion of a circuit substrate 75 is bent at a right angle with respect to the longitudinal direction of the insertion part 6 even though the circuit substrate 75 on which the image sensor 23 is mounted is a flexible substrate or a rigid substrate.

As described above, the endoscope disclosed in this specification includes an imaging device that is provided in a tip portion of an insertion part capable of being inserted into a body cavity. The imaging device includes a solid-state imaging element that photoelectrically converts imaging light incident on an image receiving surface thereof through an imaging lens, and a circuit substrate including a connecting surface facing a terminal face that is a surface opposite to the image receiving surface of the solid-state imaging element. A plurality of terminals are uniformly arranged longitudinally and laterally in a two-dimensional matrix form on the terminal face of the solid-state imaging element, the connecting surface of the circuit substrate and the terminal face of the solid-state imaging element are connected to each other through the plurality of terminals, and the total area of the plurality of terminals, which are arranged on the terminal face, occupies 10% or more of the area of an imaging area of the image receiving surface of the solid-state imaging element.

Further, the imaging device includes a prism on which the imaging light having passed through the imaging lens is incident, and the solid-state imaging element is disposed such that the image receiving surface faces a light emitting surface of the prism and is parallel to a longitudinal direction of the insertion part.

Furthermore, the circuit substrate is a rigid substrate of which bending stiffness is higher than bending stiffness of the solid-state imaging element.

Further, the imaging device includes a prism on which the imaging light having passed through the imaging lens is incident, and the solid-state imaging element is disposed such that the image receiving surface faces a light emitting surface of the prism and is parallel to a longitudinal direction of the insertion part.

Furthermore, the circuit substrate is a ceramic substrate.

The endoscope further includes a flexible wiring board which is electrically connected to the circuit substrate and to which a transmission cable is electrically connected, and the circuit substrate and the flexible wiring board are electrically connected to each other through a connector.

The endoscope further includes a flexible wiring board which is electrically connected to the circuit substrate and to which a transmission cable is electrically connected, and the circuit substrate includes a recessed portion in which an electronic component is mounted and which is provided outside a region of the circuit substrate and the flexible wiring board connected to each other.

Further, the circuit substrate includes a recessed portion in which an electronic component is mounted and which is provided in a region surrounded by a region of the circuit substrate and the flexible wiring board connected to each other through the connector.

EXPLANATION OF REFERENCES

1: endoscope system
2: endoscope
6: insertion part
10: tip portion
20A, 20B, 20C: imaging device
21: lens barrel
23: image sensor (solid-state imaging element)
22: prism
23a: terminal face
24: circuit substrate
25: image sensor connecting portion
25a: connecting surface
27: cable connecting portion
29: transmission cable
31: terminal
41: circuit substrate
41a: connecting surface
43: flexible wiring substrate
43a: substrate connecting portion
43b: cable connecting portion
61: circuit substrate
61a: connecting surface
61b: connector mounting portion
62: recessed portion
63: flexible wiring substrate
63a: substrate connecting portion
63b: cable connecting portion
65a: male connector
65b: female connector
69: connector body
71: electrode
75: circuit substrate

What is claimed is:

1. An endoscope comprising:
an imaging device that is provided in a tip portion of an insertion part capable of being inserted into a body cavity,
wherein the imaging device includes a solid-state imaging element that photoelectrically converts imaging light incident on an image receiving surface thereof through an imaging lens, and a circuit substrate including a connecting surface facing a terminal face that is a surface opposite to the image receiving surface of the solid-state imaging element,
a plurality of terminals are uniformly arranged longitudinally and laterally in a two-dimensional matrix form on the terminal face of the solid-state imaging element,
the connecting surface of the circuit substrate and the terminal face of the solid-state imaging element are connected to each other through the plurality of terminals, and
the total area of the plurality of terminals, which are arranged on the terminal face is 10% or more of the area of an imaging area of the image receiving surface of the solid-state imaging element,
wherein the circuit substrate is a rigid substrate of which bending stiffness is higher than bending stiffness of the solid-state imaging element.

2. The endoscope according to claim 1,
wherein the imaging device includes a prism on which the imaging light having passed through the imaging lens is incident, and
the solid-state imaging element is disposed such that the image receiving surface faces a light emitting surface of the prism and is parallel to a longitudinal direction of the insertion part.

3. The endoscope according to claim 2,
wherein the circuit substrate is a ceramic substrate.

4. The endoscope according to claim 3, further comprising:
a flexible wiring board which is electrically connected to the circuit substrate and to which a transmission cable is electrically connected, and
wherein the circuit substrate and the flexible wiring board are electrically connected to each other through a connector.

5. The endoscope according to claim 3, further comprising:
a flexible wiring board which is electrically connected to the circuit substrate and to which a transmission cable is electrically connected, and
wherein the circuit substrate includes a recessed portion in which an electronic component is mounted and which is provided outside a region of the circuit substrate and the flexible wiring board connected to each other.

6. The endoscope according to claim 2, further comprising:
   a flexible wiring board which is electrically connected to the circuit substrate and to which a transmission cable is electrically connected, and
   wherein the circuit substrate and the flexible wiring board are electrically connected to each other through a connector.

7. The endoscope according to claim 2, further comprising:
   a flexible wiring board which is electrically connected to the circuit substrate and to which a transmission cable is electrically connected, and
   wherein the circuit substrate includes a recessed portion in which an electronic component is mounted and which is provided outside a region of the circuit substrate and the flexible wiring board connected to each other.

8. The endoscope according to claim 1,
   wherein the circuit substrate is a ceramic substrate.

9. The endoscope according to claim 8, further comprising:
   a flexible wiring board which is electrically connected to the circuit substrate and to which a transmission cable is electrically connected, and
   wherein the circuit substrate and the flexible wiring board are electrically connected to each other through a connector.

10. The endoscope according to claim 8, further comprising:
    a flexible wiring board which is electrically connected to the circuit substrate and to which a transmission cable is electrically connected, and
    wherein the circuit substrate includes a recessed portion in which an electronic component is mounted and which is provided outside a region of the circuit substrate and the flexible wiring board connected to each other.

11. The endoscope according to claim 1, further comprising:
    a flexible wiring board which is electrically connected to the circuit substrate and to which a transmission cable is electrically connected, and
    wherein the circuit substrate and the flexible wiring board are electrically connected to each other through a connector.

12. The endoscope according to claim 11,
    wherein the circuit substrate includes a recessed portion in which an electronic component is mounted and which is provided in a region surrounded by a region of the circuit substrate and the flexible wiring board connected to each other through the connector.

13. The endoscope according to claim 1, further comprising:
    a flexible wiring board which is electrically connected to the circuit substrate and to which a transmission cable is electrically connected, and
    wherein the circuit substrate includes a recessed portion in which an electronic component is mounted and which is provided outside a region of the circuit substrate and the flexible wiring board connected to each other.

\* \* \* \* \*